United States Patent
Mark et al.

(10) Patent No.: US 8,137,320 B2
(45) Date of Patent: Mar. 20, 2012

(54) SECUREMENT FOR A SURGICAL SITE MARKER AND DEPLOYMENT DEVICE FOR SAME

(75) Inventors: Joseph L. Mark, Indianapolis, IN (US); Zachary R. Nicoson, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 218 days.

(21) Appl. No.: 12/113,625

(22) Filed: May 1, 2008

(65) Prior Publication Data

US 2008/0294092 A1    Nov. 27, 2008

Related U.S. Application Data

(60) Provisional application No. 60/915,275, filed on May 1, 2007.

(51) Int. Cl.
*A61M 5/178* (2006.01)

(52) U.S. Cl. ............... 604/167.06; 604/167.03
(58) Field of Classification Search ........... 604/167.03–167.06, 57–62, 164.11, 604/158
See application file for complete search history.

(56) References Cited

U.S. PATENT DOCUMENTS

| | | | |
|---|---|---|---|
| 5,752,970 A * | 5/1998 | Yoon | 606/185 |
| 6,027,471 A * | 2/2000 | Fallon et al. | 604/59 |
| 6,123,683 A * | 9/2000 | Propp | 604/60 |

* cited by examiner

*Primary Examiner* — Nicholas D Lucchesi
*Assistant Examiner* — Pritesh Patel
(74) *Attorney, Agent, or Firm* — Rader, Fishman & Grauer, PLLC

(57) ABSTRACT

A method of securing a biopsy marker within a biopsy site includes depositing a marker element within a biopsy site and fixing the marker element within the biopsy site by injecting a securing agent within the biopsy site. Delivery devices for delivering the securing agent to the biopsy site are also disclosed.

23 Claims, 3 Drawing Sheets

SECUREMENT FOR A SURGICAL SITE MARKER AND DEPLOYMENT DEVICE FOR SAME

CROSS-REFERENCE TO RELATED APPLICATIONS

This application claims priority to U.S. Patent Ser. No. 60/915,275, with a filing date of May 1, 2007, the contents of which are hereby incorporated by reference in its entirety.

TECHNICAL FIELD

This disclosure relates generally to securing a surgical site marker to prevent migration thereof within a biopsy site and a deployment device to be used in this endeavor.

BACKGROUND

In the diagnosis and treatment of breast cancer, it is often necessary to perform a biopsy to remove tissue samples from a suspicious mass. The suspicious mass is typically discovered during a preliminary examination involving visual examination, palpation, X-ray, magnetic resonance imaging (MRI), ultrasound imaging or other detection means.

When a suspicious mass is detected, a sample is taken by biopsy, and then tested to determine whether the mass is malignant or benign. This biopsy procedure can be performed by a variety of surgical techniques.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, and the original features of the tissue may have been removed or altered by the biopsy, it is desirable to insert one or more site markers into the surgical site to serve as a landmark for future identification of the location of the lesion.

However, one problem that arises with site markers is migration. When the site markers are typically deployed to the biopsy site, the breast is still under compression. However, when the breast is released from compression, the site marker may migrate within the site or even out of the site through a needle tract created by the biopsy device, thereby preventing a surgeon or radiologist from easily locating the precise location of the lesion or biopsied area.

BRIEF DESCRIPTION OF THE DRAWINGS

Features and advantages of the disclosure will be apparent from the following detailed description and the appended claims, taken in conjunction with the accompanying drawings, in which:

DETAILED DESCRIPTION

Figure 1:
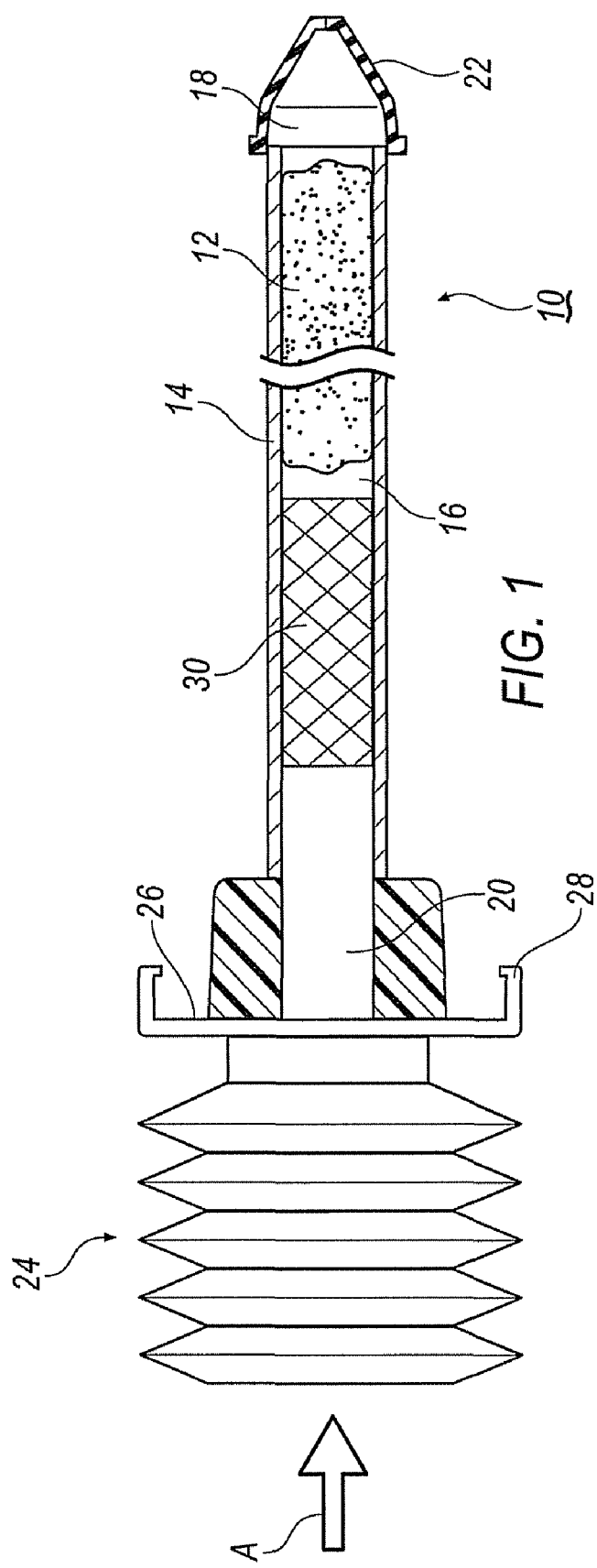
FIG. 1 is a partial cross-sectional view of a first embodiment of a securing agent deployment device.

Referring now to the drawings, exemplary approaches are shown in detail. Although the drawings represent some exemplary approaches, the drawings are not necessarily to scale and certain features may be exaggerated to better illustrate and explain the present disclosure. Further, the approaches set forth herein are not intended to be exhaustive or to otherwise limit or restrict the disclosure to the precise forms and configurations shown in the drawings and disclosed in the following detailed description.

Overview of the Disclosure

In a typical biopsy procedure, such as a breast biopsy, a patient's breast may be placed in compression. Next, a target site is biopsied using any one of a variety of biopsy devices. After the biopsy procedure, a surgeon typically deploys a site marker into the biopsy site (sometimes referred to as a biopsy cavity) formed by the biopsy procedure. The marker may be deployed using a marker deployment system, examples of which are described in co-pending U.S. application Ser. Nos. 11/238,295 and 11/305,141, the contents of which are incorporated herein by reference in their entireties.

To secure the marker in a desired location within the biopsy site, an embodiment of this disclosure includes a method of using the body's own haem (blood) as a securing/gluing agent to attach or bond the marker to a specific biopsy site or location, thereby precluding and potentially eliminating migration of the marker away from the desired biopsy site or down a needle track created by the biopsy needle.

In connection with one exemplary embodiment of the method, a haemostatic agent is injected into the biopsy site shortly after the marker is deployed into the biopsy site. The haemostatic agent causes the blood within the site to clot, thereby locking and securing the marker and tissue into place. When the breast is released from compression after the biopsy procedure is completed, the marker will remain bonded in place.

One suitable haemostatic agent is sold under the trade name Arista™, which is manufactured by Medafor, Inc. In one exemplary arrangement, the haemostatic agent is provided in a powder or slurry form to allow for rapid clotting, though other forms of a haemostatic agent may also be used.

EXEMPLARY EMBODIMENTS

FIG. 1 is a cross-sectional view of a securing agent deployment device 10 that may be used to selectively deploy a securing agent 12, such as a haemostatic agent, to a biopsy site. Deployment device 10 includes an elongated cannula 14 defining an inner lumen 16 therein. Cannula 14 is defined by a first end 18 and a second end 20. In one arrangement, a normally closed valve 22 may be secured to first end 18. In one exemplary embodiment, valve 22 is configured as a duckbill valve and is disposed around an exterior of cannula 14 at first end 18. It is understood however, that other types of normally closed valves may also be employed. It is also understood that the valve 22 may be arranged at first end 18 in other manners than what is shown in FIG. 1. For example, valve 22 may be secured within the interior of cannula 14.

An actuation portion 24 is connected to second end 20. In one arrangement, actuation portion 24 is used to deliver air to inner lumen 16, to be explained in further detail below. Positioned within inner lumen 16 is a predetermined amount of securing agent 12. In one embodiment, securing agent 12 is provided in a powder form, although it is understood that securing agent may be provided in other forms as well. For example, securing agent 12 may be provided in a slurry form, a liquid, a gel, or as a pellet or plug. A filter element 30 (to be explained below in further detail) may also be provided to position securing agent 12 within inner lumen 16.

In operation, first end 18 of deployment device 10 is inserted into a biopsy cavity. In one arrangement, elongated cannula 14 of deployment device 10 is inserted into a delivery cannula of a biopsy device or, alternatively, an introducer system that is in registration with the biopsy site. An exemplary introducer system may be found in commonly owned U.S. Pat. No. 7,347,829, the contents of which are incorporated herein by reference in its entirety. Deployment device 10 may include a mounting flange 26 from which one or more latching fingers 28 may extend. Latching fingers may be configured to cooperate with a portion of the biopsy device or a portion of the introducer system to selectively fix deployment device 10 thereto.

After first end 18 is positioned within the biopsy site, actuation portion 24, which in one exemplary embodiment is configured as a bellows bulb, is activated (in the exemplary illustrated embodiment, depressed) in the direction of arrow A. The activation forces fluid, and in one embodiment, air, into cannula 14 at second end 20 and into contact with securing agent 12. As the fluid moves through cannula 14, normally closed valve 22 is forced open, and at least a portion of securing agent 12 is deployed into the biopsy site. In one embodiment, securing agent 12 is deployed currently with a site marker (to be explained below). In another embodiment, securing agent 12 is deployed shortly after site marker is deployed to the biopsy cavity. Once deployed, securing agent 12 accelerates clotting, such that the marker element becomes fixed into position within tissue of the biopsy site and is substantially prevented from migrating within, or out of, the biopsy site.

In one arrangement, to retain securing agent 12 within cannula 14 prior to deployment, deployment device 10 may further include a filter element 30 positioned between first end 18 and second end 20. Securing agent 12 may be positioned between filter element 30 and first end 18. Filter element 30 may be semi-permeable such that securing agent 12 is substantially prevented from passing therethough, but fluid is permitted to pass therethrough. In one embodiment, filter element 30 is an open cell foam material.

Figure 2:
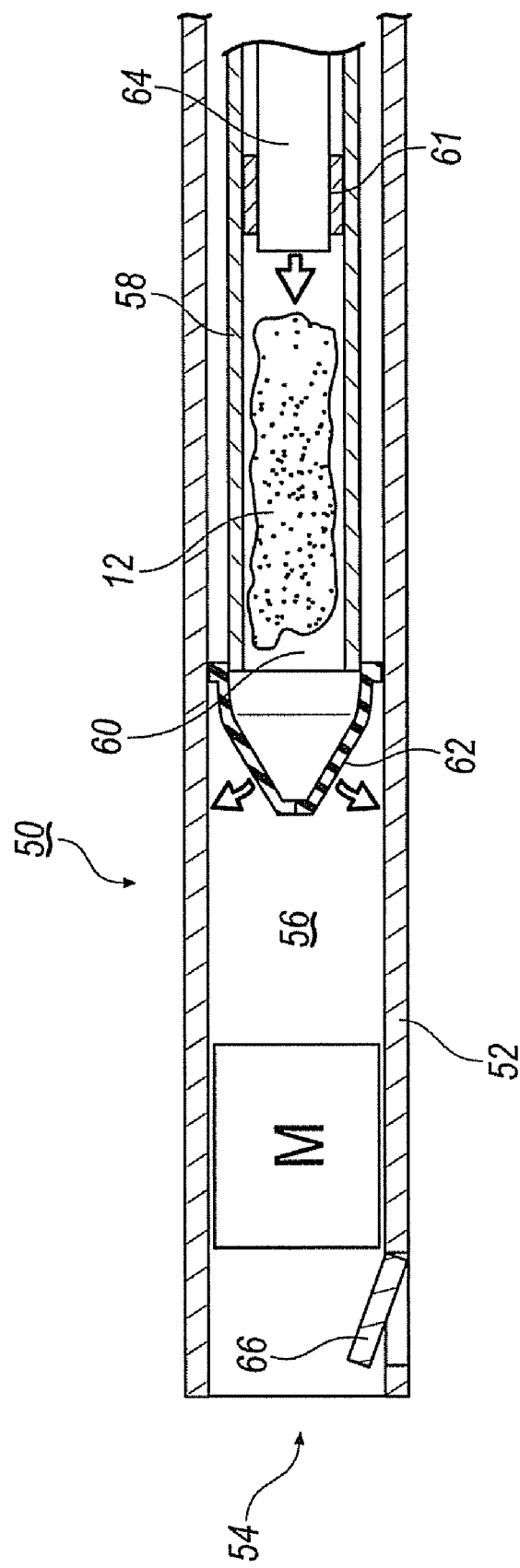
FIG. 2 is a second embodiment of a securing agent and marker deployment device.

In another exemplary approach, both marker M and securing agent 12 may be deployed by a single deployment device 50. Referring to FIG. 2, deployment device 50 will now be described.

Deployment device 50 includes an outer cannula 52 having an open distal end 54 and defining a lumen 56 therein. An inner cannula 58 is positioned within outer cannula 52. Inner cannula 58 includes a distal end 60 to which a normally closed valve 62 (such as a duckbill valve) is secured. An actuation member 64, which is selectively slidable within inner cannula 58, is further provided. In one embodiment, a seal member 61 may be provided within inner cannula 58, through which actuation member 64 passes. Seal member 61 serves to prevent securing material 12 from escaping through a proximal end of inner cannula 58.

In operation, securing agent 12 is retained within inner cannula 58 and one or more markers M are positioned within lumen 56 of outer cannula 52. Distal end 54 of outer cannula 52 is positioned at the target site. Outer cannula 52 may be delivered to the biopsy site through a biopsy delivery cannula or an introducer assembly, as described above. In one embodiment, marker M may be temporarily retained adjacent distal end 54 by a deformable retaining tab 66.

To deploy securing agent 12 and marker M, actuation member 64 (which may be a plunger) is activated. Actuation member 64 is moved distally, pushing at least a portion of securing agent 12 through distal end 60 of inner cannula 58, thereby opening normally closed valve member 62. Actuation member 64 continues through inner cannula 58 and comes into contact with marker M, thereby pushing both securing agent 12 and marker M past retaining tab 66 and into the biopsy site with a single device and substantially simultaneously.

In another embodiment, securing agent 12 may be provided in plug form that is adhered to at least a portion of marker M. In this configuration, inner cannula 58 may not be needed. Instead, only actuation member 64 is used to eject marker M and attached securing agent 12 plug from outer cannula. In yet another embodiment, securing agent 12 is provided as a separate pellet from marker M. In this embodiment, actuation member 64 may push out both marker M and the separate pellet of securing agent 12 to the biopsy site.

In one arrangement, actuation member 64 is a plunger. It may be desirable that actuation member 64 be sized so as to extend a predetermined distance past distal end 54 of outer cannula 52 to insure that marker M and securing agent 12 are fully deployed into the biopsy site.

Figure 3:
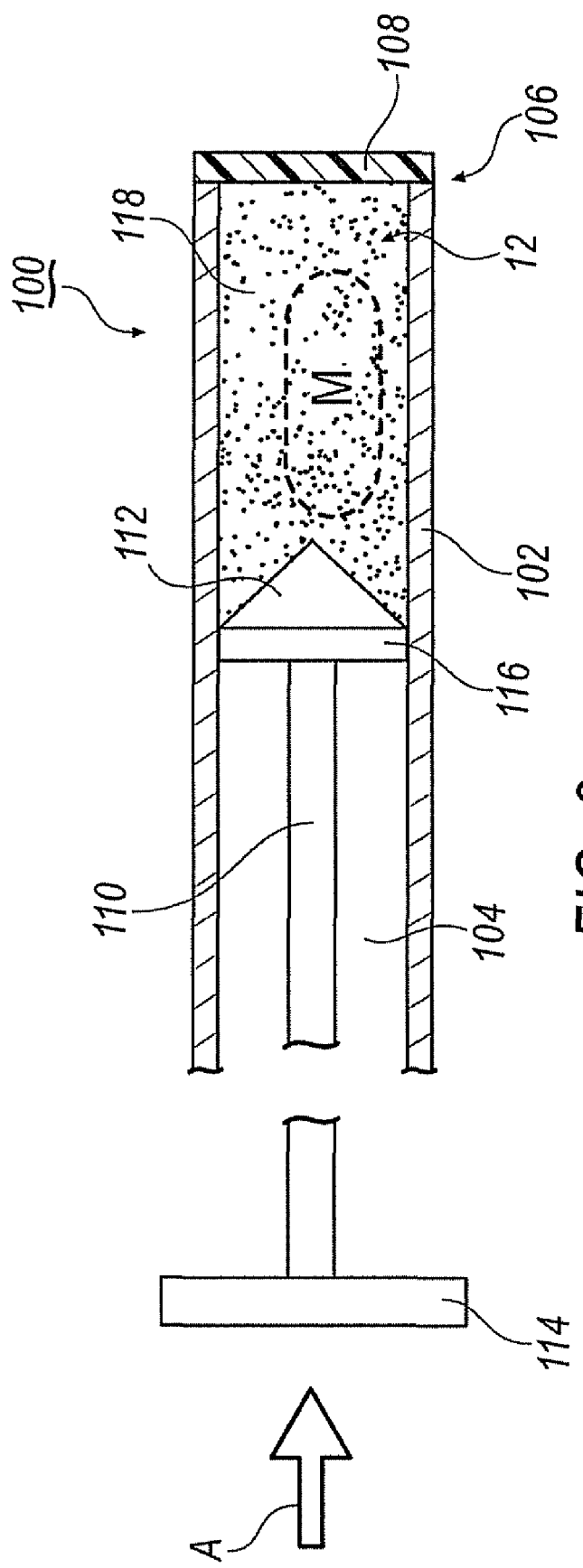
FIG. 3 is a third embodiment of a securing agent deployment device.

Another embodiment of a securing agent deployment device 100 is shown in FIG. 3. FIG. 3 is a partial cross-sectional view of securing agent deployment device 100 that may be used to selectively deploy a securing agent 12, such as for example, a haemostatic agent, to a biopsy site. Deployment device 100 includes an elongated cannula 102 defining an inner lumen 104 therein. Cannula 102 includes a first end 106 and a second end (not shown).

Attached to first end 106 is a film or cap member 108. Film or cap member 108 temporarily closes first end 106, as will be explained below. In one embodiment film or cap member 106 is constructed of a bioabsorbable material. In another embodiment, film or cap member 106 is a heat shrinkable material that is deformed around first end 106 to temporarily close of first end 106.

Disposed within inner lumen 104 is an actuation device 110 having a distal end and proximal end. In one embodiment, actuation device 110 is a plunger having a piercing tip 112 disposed at the distal end and an actuation member 114 formed at the proximal end. Disposed adjacent to piercing tip 112 is a seal member 116 that is sized to have a size and shape that generally corresponds to inner lumen 104, but permits actuation device 110 to slide within inner lumen 104. While actuation device 110 is depicted with a piercing tip 112 at the distal end, it is understood that piercing tip 112 is optional. For example, piercing tip 112 may be eliminated entirely.

Prior to operation, actuation device 110 is in a retracted position (shown in FIG. 3), whereby the distal end of actuation device 110 and the film or cap member 108 cooperate with inner lumen 104 to form cavity 118 into which securing material 12 is positioned. Next, the deployment device 100 is positioned such that a distal end thereof is positioned within the biopsy site. Similar to deployment devices 10 and 50, deployment device 100 may be positioned in a delivery cannula or an introducer device to deliver distal end 106 to the biopsy site.

To deploy securing agent 12, actuation device 110 is moved distally in the direction of arrow A by pressing on actuation member 114. In the embodiment shown in FIG. 3, piercing tip 112 may cooperate with seal member 116 to push securing agent 12 towards film or cap member 108. Actuation device 110 may be sized so as to be at least slightly longer than the length of cannula 102 such that when actuation device 110 is fully deployed, piercing tip 112 (or distal end of actuation device 110) will rupture or dislodge film or cap 108 from distal end 106 of cannula 102 and expel securing agent 12 into the biopsy site. In another embodiment wherein the film or cap 108 is heat shrunk onto distal end 106, the body heat within the cavity will dislodge film or cap 108.

In another embodiment, one or more site markers M (FIG. 3, shown in phantom) may also be positioned within cavity 118 such that when actuation device 110 is activated, both securing agent 12 and marker M will be deployed generally simultaneously to the biopsy site.

While the present disclosure has been particularly shown and described with reference to the foregoing embodiments, it should be understood by those skilled in the art that various alternatives to the embodiments of the disclosure described herein may be employed in practicing the disclosure without departing from the spirit and scope of the disclosure as defined in the following claims. It is intended that the following claims define the scope of the invention and embodiments within the scope of these claims and their equivalents be covered thereby. This description of the disclosure should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

What is claimed is:

1. A delivery device, comprising:
   a cannula defining an inner lumen therein, the cannula having a proximal end and a distal end;
   a valve member secured to the cannula, wherein the valve member is secured generally toward the distal end of the cannula;
   an actuation portion connected to the proximal end of the cannula;
   a semi-permeable filter element positioned within the cannula between the valve member and the actuation portion, the filter element cooperating to form a cavity between the valve member and the filter element;
   wherein the cavity is configured to hold a securing agent and wherein the actuation portion may be selectively depressed to cause a fluid to flow through filter element and force the securing agent through the valve member.

2. The device of claim 1, wherein the valve member is a normally closed valve member.

3. The device of claim 2, wherein the valve member is a duckbill valve.

4. The device of claim 1, wherein the valve member is secured to the exterior of the distal end of the cannula.

5. The device of claim 1, wherein the valve member is secured to a portion of the interior of the cannula, so as to be spaced inwardly from a distal end of the cannula.

6. The device of claim 1, wherein the filter element is an open cell foam material.

7. The device of claim 1, wherein the actuation portion is a bellows-style plunger.

8. The device of claim 1, further comprising at least one retaining latch.

9. The device of claim 1, wherein the actuation portion is a plunger.

10. The device of claim , further comprising a seal member disposed around a portion of the plunger.

11. The device of claim 1, further comprising a selectively openable cap member disposed over the distal end.

12. The device of claim 11, wherein the actuation portion is a plunger and wherein a piercing element is attached to a distal end of the plunger.

13. The device of claim 11, wherein the cap member is constructed of bioabsorbable material.

14. The device of claim 11, wherein the cap member is a film.

15. The device of claim 11, wherein the film is a heat shrinkable material.

16. The device of claim 1 further comprising a pushrod.

17. The device of claim 16, further comprising a seal member disposed around a portion of the pushrod and sized to permit pushrod to slide therethrough.

18. The device of claim 1, wherein the cavity holds a marker element.

19. The device of claim 18, wherein the securing agent is secured to at least a portion of the marker element.

20. The device of claim 18, wherein the securing agent is in the form of a pellet.

21. A device comprising:
   an outer cannula having an open distal end;
   an inner cannula disposable within the outer cannula and having a selectively openable distal end; and
   an actuation member disposed in the inner cannula;
   wherein the outer cannula is configured to house a marker element distally of the inner cannula and the inner cannula is configured to house a securing agent; and
   wherein the actuation member is configured to extend through the inner cannula and the outer cannula such that the actuation member contacts the securing agent and the marker element thereby forcing the securing agent and the marker element out of the open distal end of the cannula.

22. A device, comprising:
   a cannula defining an inner lumen therein;
   a cap member attached to a distal end of the cannula and generally closing off the inner lumen; and
   an actuation member slidably disposed within the inner lumen;
   wherein the cap member and the actuation member cooperate with the inner lumen to define a cavity configured to receive a securing agent; and
   wherein the actuation member is selectively movable distally toward the cap member to rupture the cap member from the distal end of the cannula to expel the securing agent from the cannula.

23. The device of claim 1, further including at least one mounting flange fixedly secured to the delivery device, wherein the mounting flange is configured to engage at least one of a separate introducer and a delivery cannula so as to selectively fix the delivery device thereto.

* * * * *